United States Patent
Sale et al.

(10) Patent No.: US 10,901,117 B2
(45) Date of Patent: Jan. 26, 2021

(54) DEVICES AND METHODS FOR MEASURING TEMPERATURE, OXIDATION REDUCTION POTENTIAL, AND WATER-LEVEL WITHIN A SUBSURFACE FORMATION

(71) Applicant: Colorado State University Research Foundation, Fort Collins, CO (US)

(72) Inventors: Thomas C. Sale, Bellvue, CO (US); Jay M. Ham, Fort Collins, CO (US); William Samuel Gallo, Fort Collins, CO (US); Kayvan Karimi Askarani, Fort Collins, CO (US); Zachary Scott Ferrie, Fort Collins, CO (US); Joseph Scalia, IV, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 16/600,946

(22) Filed: Oct. 14, 2019

(65) Prior Publication Data
US 2020/0116894 A1 Apr. 16, 2020

Related U.S. Application Data

(60) Provisional application No. 62/745,803, filed on Oct. 15, 2018, provisional application No. 62/745,898, filed on Oct. 15, 2018.

(51) Int. Cl.
*G01V 11/00* (2006.01)
*H04Q 9/00* (2006.01)
*G01N 33/24* (2006.01)

(52) U.S. Cl.
CPC .......... *G01V 11/002* (2013.01); *G01N 33/24* (2013.01); *G01N 33/246* (2013.01); *H04Q 9/00* (2013.01);
(Continued)

(58) Field of Classification Search
CPC ...................................................... G01N 27/00
See application file for complete search history.

(56) References Cited

U.S. PATENT DOCUMENTS 6,356,205 B1 * 3/2002 Salvo .................... G01N 33/18
210/143
10,094,719 B2 10/2018 Sale et al.
(Continued)

OTHER PUBLICATIONS

Hunt, Brian et al., "Groundwater-Level Monitoring Program: Example from the Barton Springs Segment of the Edwards Aquifer, Central Texas." Texas Water Monitoring Congress 2004, pp. 1-10. (Year: 2004).*

*Primary Examiner* — Nabil H Syed
*Assistant Examiner* — Cal J Eustaquio
(74) *Attorney, Agent, or Firm* — Polsinelli PC

(57) ABSTRACT

A subsurface monitoring system and method is provided that includes a sensor array and a monitoring system in communication with the array. The sensor array may include several sensors, such as subsurface temperature sensors, water-level sensors, and oxidation reduction potential sensors may be disposed in a vertical and/or horizontal fence through the subsurface of the monitored site. The sensor array may measure, collect, and analyze the subsurface conditions and provide the measurements to a monitoring system. The monitoring system may provide access the measurements via a user interface for analysis of the measurements. In addition, the monitoring system may process the measurements to generate one or more graphs of information for better understanding of the conditions of the subsurface of the monitored site.

18 Claims, 11 Drawing Sheets

(52) U.S. Cl.
CPC ... *H04Q 2209/30* (2013.01); *H04Q 2209/886* (2013.01)

(56) References Cited

U.S. PATENT DOCUMENTS

| | | | |
|---|---|---|---|
| 10,113,990 B2 | 10/2018 | Burge et al. | |
| 2003/0209653 A1* | 11/2003 | Feldsine | G01N 21/76 250/214 R |
| 2007/0093974 A1* | 4/2007 | Hoogenboom | G06F 16/95 702/35 |
| 2012/0014750 A1* | 1/2012 | Paranhos Torres | B09C 1/00 405/128.75 |
| 2014/0138308 A1* | 5/2014 | Elger | C02F 3/006 210/605 |

* cited by examiner

DEVICES AND METHODS FOR MEASURING TEMPERATURE, OXIDATION REDUCTION POTENTIAL, AND WATER-LEVEL WITHIN A SUBSURFACE FORMATION

CROSS REFERENCE TO RELATED APPLICATION

This application claims priority from U.S. provisional patent application Ser. No. 62/745,803, entitled "3G Dashboard" filed on Oct. 15, 2018, and from U.S. provisional patent application Ser. No. 62/745,898, entitled "3G Monitoring Hardware" filed on Oct. 15, 2018, the entirety of both of which is incorporated by reference herein.

FIELD OF THE INVENTION

This application relates to devices and methods for subsurface monitoring. In particular, this application relates to methods and devices of measuring, collecting, and analyzing subsurface temperature, water-level, and oxidation reduction data to obtain an understanding of subsurface conditions.

BACKGROUND OF THE INVENTION

An ongoing environmental challenge is managing the legacy of anthropogenic activities that have resulted in the contamination of groundwater, surface water, soil, sediments and/or soil gas in subsurface source zones and plumes. Source zones may be defined as saturated or unsaturated subsurface regions containing hazardous substances, pollutants, or reactive materials that may act as reservoirs that sustain a reactive material plume in groundwater, surface water, or air or may act as sources for direct exposure. These source zones may include sorbed and aqueous-phase reactive materials as well as non-aqueous reactive materials such as solids or nonaqueous phase liquids (NAPLs). Plumes are zones about source zones where contaminants have moved to, from source zones, via the flow of fluids and/or diffusion.

The monitoring of materials introduced into subsurface formations poses an ongoing challenge for the environmental management of various industrial facilities including waste collection, product refining, product transportation, and storage facilities. Typically, monitoring includes deploying groundwater professionals to potentially contaminated sites to collect groundwater samples and water levels from monitoring wells. The samples are then shipped to laboratories, analyses are compiled, reports may be submitted and analysis of the reports may be conducted. This process may take several months and may cost several thousand dollars to complete. Further, blended aqueous concentrations from monitoring wells with large open intervals may leave the measurements ignorant with respect to NAPLs, sorbed phases, vapor phases, contaminants in low permeability zones, implications of transient groundwater flow, governing redox conditions, and rates of natural assimilation of contaminants. Also, vertical hydraulic gradient across open sections of wells and the conveyance of atmospheric gases into the sampled intervals through open well casings can add largely indiscernible data biases that can be difficult to recognize.

A need exists for a robust method and devices for monitoring subsurface conditions containing hazardous substances, pollutants, or reactive materials in groundwater, surface water, or air or may act as sources for direct exposure. Such a method may be used to monitor the degree of contamination of a subsurface formation, to assess the rate of degradation of the reactive materials, resolve the areal and vertical extent of contaminants, and assess the effectiveness of remedial actions addressing subsurface contamination.

SUMMARY OF THE INVENTION

In an aspect of the present disclosure may include a device for monitoring subsurface conditions. The device may include a data collector comprising at least one hardware processor and at least one memory to store executable instructions and a plurality of sensors in communication with the data collector deployed in a subsurface of a monitored area, each of the plurality of sensors obtaining an environmental measurement of the subsurface of the monitored area and transmitting, via a communication wire, the environmental measurement to the data collector. A subset of the plurality of sensors may be grouped together as a group of sensors comprising a temperature sensor, a water-level sensor, and an oxidation reduction potential sensor. The instructions, when executed by the at least one processor, are configured to package a plurality of the environmental measurements received from the plurality of sensors into one or more transmission packets and wirelessly transmit the one or more transmission packets to a monitoring system, the monitoring system in communication with a user interface for displaying the environmental measurements.

Another aspect may include a method for monitoring subsurface conditions at a pollution site. The method may include the operation of receiving, via a plurality of sensors in communication with a data collector of a sensor array deployed in a subsurface of a monitored area, a plurality of environmental measurements of the subsurface of the monitored area, each of the plurality of sensors obtaining a corresponding environmental measurement of the subsurface of the monitored area and transmitting, via a communication wire, the environmental measurement to the data collector, wherein a subset of the plurality of sensors are grouped together as a group of sensors comprising a temperature sensor, a water-level sensor, and an oxidation reduction potential sensor. The method may further include the operations of generating one or more visualizations of the plurality of environmental measurements for display on a display device and transmitting, to a computing device and via a network connection, the one or more visualizations of the plurality of environmental measurements for display in a user interface executed by the computing device.

Yet another aspect of the present disclosure may include a system comprising a sensor array deployed at a monitored area and a monitoring system of a computing network. The sensor array may include a data collector comprising a wireless communication unit and a plurality of sensors in communication with the data collector via a communication wire disposed within a conduit, each of the plurality of sensors obtaining an environmental measurement of the subsurface of the monitored area and transmitting the environmental measurement to the data collector, the plurality of sensors comprising a temperature sensor, a water-level sensor, and an oxidation reduction potential sensor. The monitoring system may include a processor and at least one memory to store instructions that are configured to, when executed by the processor to receive, via the wireless communication unit of the data collector, the environmental measurement of the subsurface of the monitored area, generate one or more visualizations of the environmental measurement for display on a display device, and transmit, to a computing device and via a network connection, the one or more visualizations of the environmental measurement for display in a user interface executed by the computing device.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

The following figures illustrate various aspects of the disclosure.

Corresponding reference characters indicate corresponding elements among the views of the drawings. The headings used in the figures should not be interpreted to limit the scope of the claims.

DETAILED DESCRIPTION

Figure 1A:
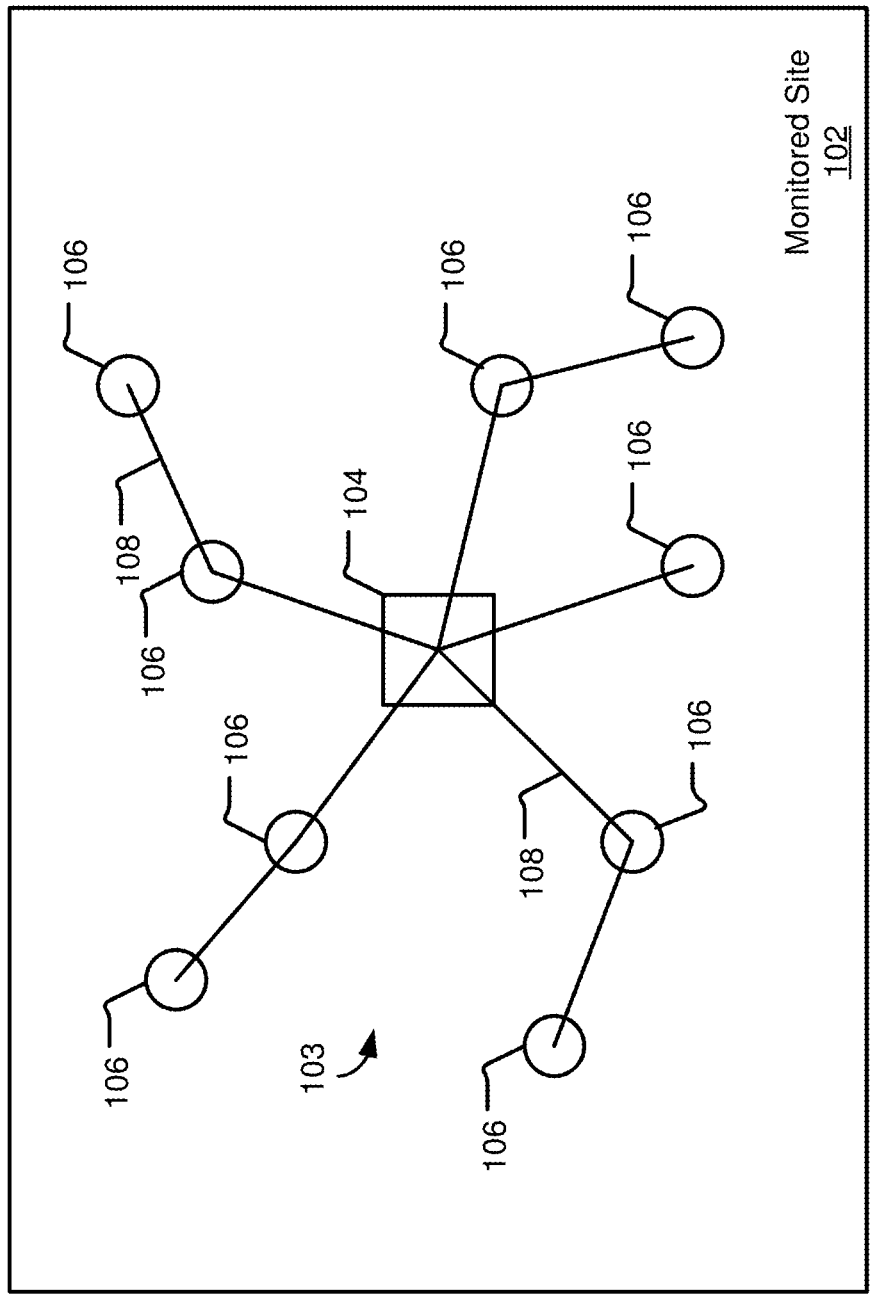
FIGS. 1A and 1B are schematic diagrams of a sensor array installed within a subsurface of a monitored site.

In various aspects, the present disclosure provides systems and methods for monitoring conditions of a subsurface area, perhaps pertaining to a potentially polluted source zone. In one particular instance, the present disclosure relates to methods and devices of measuring, collecting, and analyzing subsurface temperature, water-level, and oxidation reduction to obtain an understanding of subsurface conditions of the source zone. One or more sensor arrays may be deployed in the monitored zone to obtain the various measurements of conditions of the zone. In one particular instance, the sensor array may include multiple groups of sensors located throughout the monitored zone to create a vertical and/or horizontal monitoring fences corresponding to one or more monitoring wells within the monitored zone.

The group of sensors may include a temperature sensor, a water-level sensor, an oxidation reduction sensor, a pH-measurement sensor, and the like. Each group of sensors may provide measurements, readings, information, or other data to a centralized data acquisition module or component. In one example, multiple groups of sensors may utilize a single communication wire to provide the obtained measurement data to the data acquisition module utilizing an addressing scheme for transmission of measurement data. In another example, groups of sensors may include a dedicated or single communication wire over which the measurement data may be transmitted to the data acquisition component. The communication wires of the sensor array may be enclosed within a conduit to protect the communication wires from damage due to the conditions of the monitored site.

The data acquisition component of the deployed sensor array may receive the measurement data from the sensors, package the measurement data, process the measurement data, and/or transmit the measurement data to a monitoring system. In one example, the measurement data may be transmitted wirelessly to the monitoring system, which may be embodied within a cloud computing environment or other computing environment supported wireless communications. The data acquisition component of the sensor array may also obtain or receive information or data associated with operating conditions of the components of the sensor array, such as power levels, wireless signal strengths, operability of sensors, and the like. The operational data of the sensor array may also be transmitted to the monitoring system by the data acquisition component.

The monitoring system may receive the sensor data and/or operational data from the sensor array and process the data into one or more models, graphs, charts, or other visual displays of the received information. In addition, a user interface executed on a computing device, such as a user's computing device, may connect to or otherwise communicate with the monitoring system to receive the raw sensor data, the operational information of the sensor array, and/or the processed data. The user interface may display the information on a display device of the user's computing device such that the user may observe the sensor array information. The computing device may communicate with the monitoring system via a wired or wireless connection. Through the display of the sensor array data, the user may obtain an understanding of one or more conditions of the monitored zone via the user interface. This may remove the need for a monitoring technician to visit the monitored zone and collect physical samples from the site. As such, the collection, processing, and displaying of the condition data of the monitored site may provide a more advanced understanding of the current and past conditions of the monitored zone while reducing the time invested and cost for the collection of the data.

Figure 1B:
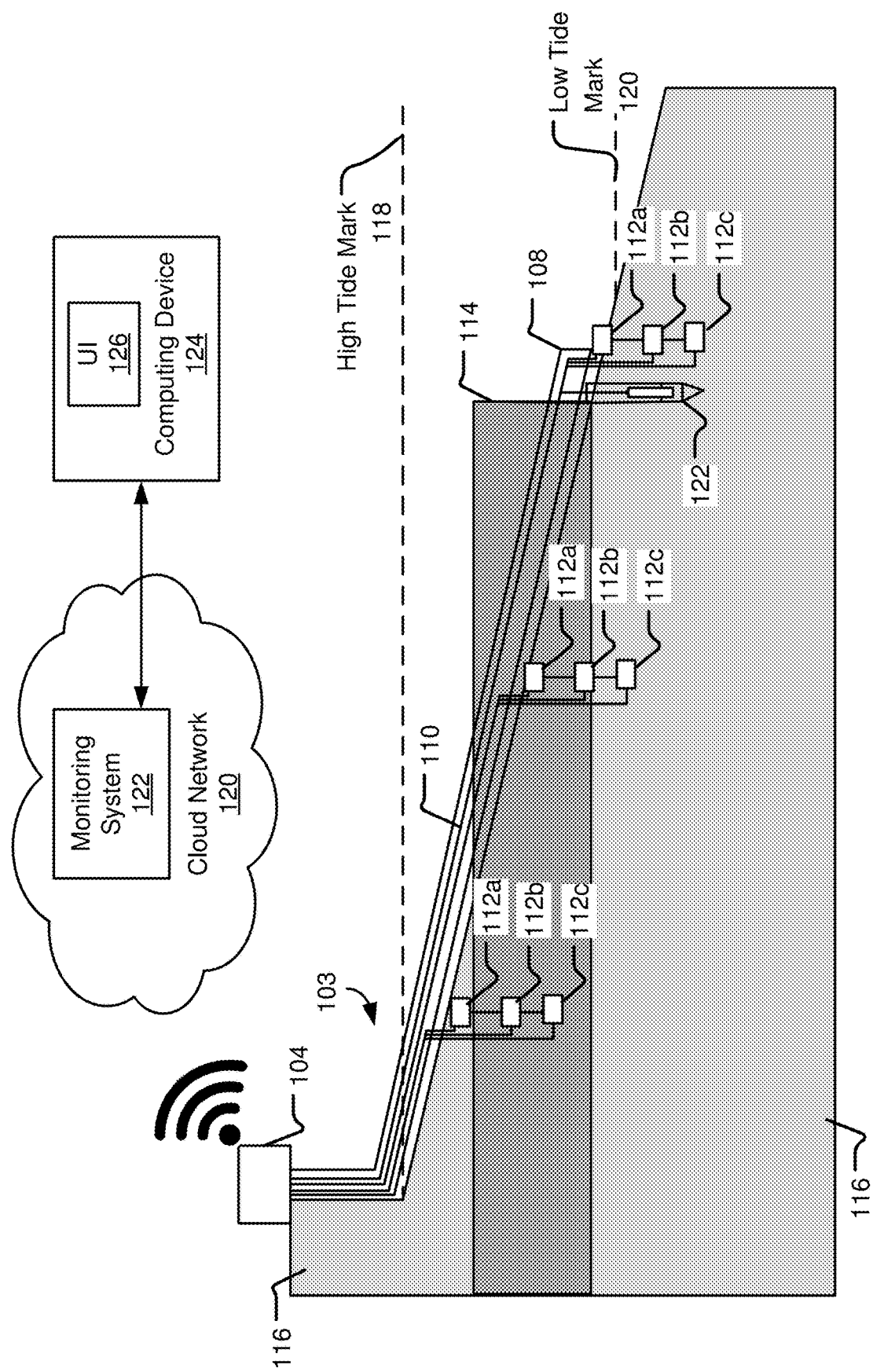

FIGS. 1A and 1B are schematic diagrams of one or more sensor arrays installed within a subsurface of a monitored site. In particular, FIG. 1A illustrates an overhead view of a monitored site 102 with a sensor array 103 disposed in a plurality of monitor wells 106 around the monitored site 102. The sensor array 103 includes a data acquisition component 104 from which one or more conduits 108 extend to the various monitoring wells 106 of the site 102. As described in more detail below, the sensor array 103 may provide vertical and horizontal monitoring fences throughout the monitored site 102. For example, the sensor array 103 may include additional conduits 108 extending vertically down one or more of the monitoring wells 106, as illustrated in FIG. 1B. FIG. 1B illustrates a cross-section view of the monitored site 102 including a sensor array 103 which may extend both vertically and horizontally into a monitoring well 106. In general, the sensor array 103 may be deployed in the monitored site 102 to measure aspects of the subsurface of the monitored site 102, such as temperature of subsurface water, water levels, oxidation-reduction potential (ORP), and the like. The sensor array 103 provides continuous, real-time monitoring of the site 102 through synergistic data sets that uniquely characterize the status of the subsurface settings as compared to measuring individual parameters using conventional groundwater monitoring techniques.

As shown in FIGS. 1A and 1B, the sensor array 103 may include groups of sensors 112 attached to a data acquisition component 104 via one or more communication wires 110. In general, the sensors 112 obtain some measurement of the conditions of the subsurface of the site 102 and provide the measurements to the data acquisition component 104 via the communication wires 110. Sensors 112 of the sensor array 103 may be deployed in horizontal and/or vertical strings to form vertical and/or horizontal monitoring fences that can include multiple vertical (transects and longsects) and/or horizontal planes of monitoring through groundwater, plumes, vapor plumes, and/or source zones at the monitored site 102. Applications of the sensor array 103 may be applied in ground liquids, gases in equilibrium with fluids, and subsurface settings including groundwater, sediments, soils, rock, and soil gas. Application in field, laboratory, and above ground environments may also be utilized.

In the example illustrated in FIG. 1B, the sensor array 103 is deployed in a subsurface environment that includes a subsurface fluid environment 116 that includes a nonaqueous phase liquids (NAPLs) zone 114. The sensor array 103 may be deployed in this environment to measure characteristics or aspects of the NAPL zone 114 of the subsurface 116 (as well as other portions of the subsurface 116), including but not limited to, temperature of subsurface water, water levels, oxidation-reduction potential (ORP), soil moisture, soil pH, and the like. To obtain the measurements of the subsurface 116, multiple groups of sensors 112, each configured to obtain an aspect or characteristic of the subsurface 116, are located in the subsurface 116, such as through a monitoring well 104. In the example shown, sensor 112a may be a temperature sensor for measuring the temperature of subsurface water 116, sensor 112b may be a water level sensor, and sensor 112c may be an ORP sensor. Multiple instances of the group of sensors 112 may be deployed in the subsurface 116 at varying depths. In one instance, at least one group of sensors 112 may be deployed between a high tide mark 118 and a low tide mark 120 of the subsurface water 116, although other depths within the subsurface 116 are contemplated.

Figure 2:
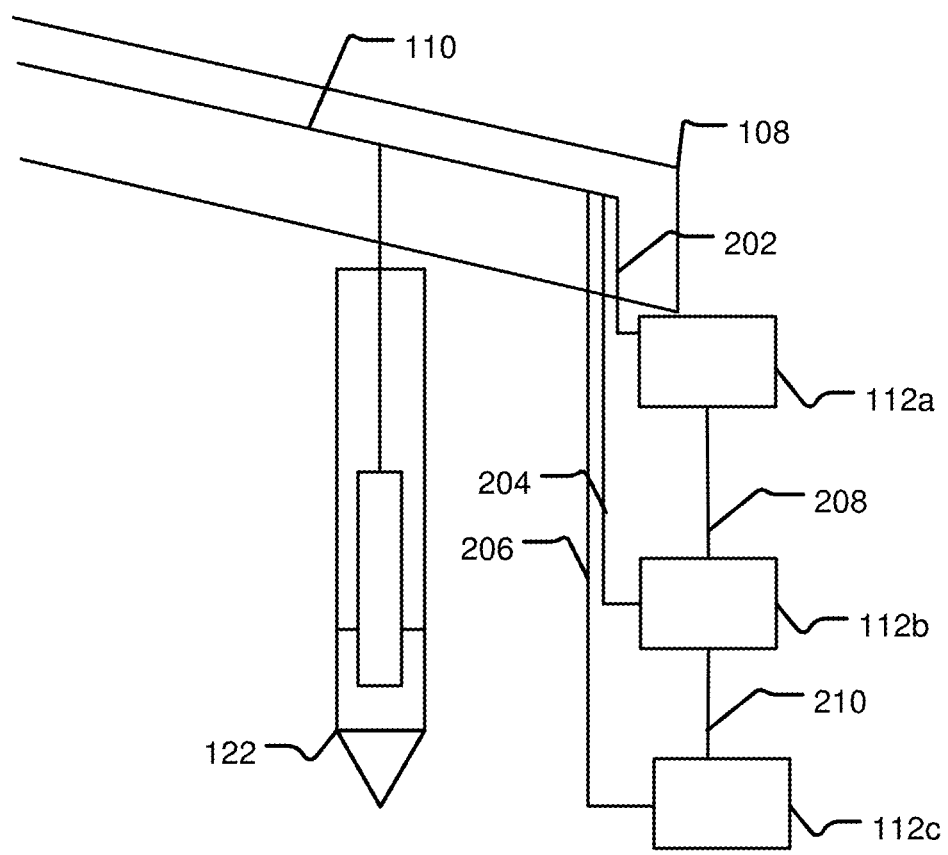
FIG. 2 is a schematic representation of a sensor module of a subsurface sensor array installed within a subsurface formation.

FIG. 2 is a schematic representation of a group of sensors 112 of a subsurface sensor array 103 deployed within a subsurface formation. As shown, sensor 112a, sensor 112b, and sensor 112c are included in the sensor group, although additional or fewer sensors may be included in the grouping. Each sensor may be configured to obtain a measurement of a condition, characteristic, or aspect of the subsurface 116. Further, each sensor 112 may connect to the data acquisition component 104 via a communication wire 110. In particular, sensor 112a may connect to communication wire 110 via sensor lead 202, sensor 112b may connection to communication wire 110 via sensor lead 204, and sensor 112c may connection to communication wire 110 via sensor lead 206. Each sensor 112a-c may transmit a respective sensor measurement or other communication on the corresponding sensor lead 202-206 for transmission along communication wire 110 to the data acquisition component 104. In one example of the sensor array 103, each sensor group 112 may be connected to a respective communication wire 110 separate from other sensor groups for transmission of sensor information to the data acquisition component 104 via the communication wire 110. In another instance, a single communication wire 110 may be included in the sensor array 103 to transmit sensor data or information from each sensor of the array. In this instance, individual sensors 112a-112c may include a unique address and data transmitted by the sensor may be addressed using the unique address. The addressing of the sensor data is described in more detail below.

A conduit 108 may extend from the data acquisition component 104 and support the various sensor groups 112 included in the sensor array 103. In some instances, the conduit 108 may be hollow such that the communication wires 110 of the array 103 are housed within the conduit 103. The sensors 112a-112c of each sensor group may be connected in a vertical stack such that a top sensor 112a may be connected to the conduit 103, a second sensor 112b may be connected to sensor 112a via connection 208, a third sensor 112c may be connected to sensor 112b via connection 210, and so on. Sensor leads 202-206 may extend from a respective sensor 112a-c through an outer wall of conduit 103 for transmission of data and signals to the data acquisition component 104.

In some instances, each sensor of the sensor array 103 may be encased in a chemically resistant clear epoxy to protect each sensor from damage from the subsurface environment 116. Communication wires 110 and/or sensor leads 202-206 may include a chemically resistant wire coating (such as Teflon) and placed within the conduit to protect the wires from physical and chemical damage. Conduit 103 may include a vinyl tube coated with a chemically resistant material and, in some instances, a grout or other filling material may be injected into the interior of the conduit 103 to further protect the communication wires 110 within. Further, in some instances, one or more sensors 112a-c may be placed inside conduit 103 to limit direct contact between the sensors 112a-c and chemicals in a monitored area. An additional benefit of locating sensors 112a-c inside the conduit 103 is to reduce the potential for sensor damage during installation or placement within the subsurface material 116. Other materials and designs are also contemplated for use with the sensor array 103 described herein.

Through the sensor array 103 disposed at the monitored site 102 to form vertical and/or horizontal monitoring fences that can include multiple vertical (transects and longsects) and/or horizontal planes of monitoring, several measurements of the conditions at the site 102 may be obtained. One such measurement includes an ORP sensor 112a that measures the oxidation-reduction potential of the ground water. ORP measurements generally include a working electrode, a counter or reference electrode, and a voltage measurement device. A preference is noted for high impedance voltage measurement devices. Sensor 112a may, in some instances, operate as the working electrode for the ORP sensor. As such, sensor 112a may include a nonreactive electrode (such as an electrode composed of titanium mesh with iridium oxide coating) and a temperature sensor. The working electrodes may be placed at a position where ORP measurements are to be made with the working electrode in direct contact with the monitored media. In the example shown in FIG. 1B, sensors 112a may be working electrodes for ORP measurements that obtain measurements at various levels within the groundwater 116. The sensors 112a may be placed such that at least one working electrode lies within the NAPL zone 114 to obtain an ORP measurement of the NAPL zone for the monitored site 102.

The sensor array 103 may also include a reference electrode 122 for use in ORP measurements. The reference electrode 122 may include a fixed potential and multiple working electrodes may be compared to a single reference electrode 122. The reference electrode 122 may be placed in a location with electrical continuity between the working electrode 112a and the reference electrode 122. Another option for deploying the reference electrode 122 is to surround the reference electrode 122 in a media that precludes wetting of the electrode by nonaqueous phase liquids. The reference electrode 122 illustrated in FIGS. 1B and 2 is encased in a tube that is filled with such a media to prevent wetting. Other reference electrode 122 constructions for ORP measurement systems are similarly contemplated for use with the sensor array 103.

Sensor 112b may be a water level sensor that provides a measurement of subsurface groundwater level. Through various vertical and/or horizontal monitoring fences of the sensor array 103 that include water level sensors, a magnitude and direction of groundwater flow may be determined for the monitored site 102. In some instances, the water level sensors 112b may be unvented pressure measurement devices to reduce potential errors in the measurements introduced by water condensation in vent lines. However, other types of water level sensors may also be used. For example, water level sensors 112b may be unvented pressure transducers in environments in which the effect of barometric pressure changes may be common to all pressure measurements. Further, multiple water level sensors 112b may be utilized and the results from which may be compared and contracted to gain an understanding of an estimated subsurface water level. Water level sensors 112b may be placed in monitoring wells 106 or directly in subsurface soil/water environments 116 as part of the sensor array 103 disposed at the monitored site 102.

In addition, sensor 112c may be a temperature sensor for measuring the temperature of the subsurface environment 116 at or near the location of the temperature sensor 112c. In some instances, temperature sensor 112c may include a thermal couple encased in a chemically resistant media (such as an epoxy) to prevent damages to the sensor by chemicals in the subsurface region 116 or corrosion by water. Further, a subsurface heating element (such as a heat trace wire or the like) may be collocated with the temperature sensor 112c. Pulse heating and measurement of temperatures may be used to acquire thermal properties of the monitored media 116.

Additional or fewer sensors may also be included in the sensor array 103. For example, sensor group 112 of FIG. 1B may include additional sensors connected to sensors 112a-c in a similar manner as the illustrated sensors. Further, the order of the sensors 112a-c of the sensor group may vary from sensor group to sensor group along the sensor array 103. For example, the ORP sensor may be sensor 112b or sensor 112c, water level sensor may be sensor 112a or sensor 112c, or temperature sensor may be sensor 112a or sensor 112b in the various sensor groups of the sensor array 103. Also, reference electrode 122 may be located at any position along the sensor array 103 for use in reference for ORP measurements. Additional sensors of the sensor array 103 may include a sensor to measure moisture in a soil environment 116 and/or a sensor to measure the pH level of the environment 116. The sensor array 103 may therefore include various configurations of sensors and sensor locations to provide measurements of the subsurface 116 of the monitored site 102 at various locations. Further still, one or more above-surface sensors may be included on and/or incorporated with the sensor array 103. For example, a barometric sensor may be included in the sensor array near or on the data acquisition component 104 for measuring the atmospheric pressure at the monitored site 102. Other environmental or meteorological sensors may also be included located at the surface of the monitored site 102 and in communication with the data acquisition component 104.

As mentioned above, the sensors 112 of the sensor array 103 provide measurement signals, data, and/or information of the monitored site 102 to the data acquisition component 104. The sensor information may be provided to the data acquisition component 104 via one or more communication wires 110 extending contained within the conduit 108. The data acquisition component 104 may receive and process the provided data and information from the sensors 112 of the sensor array 103 and, in some instances, provide the data to a centralized monitoring system 122 through a wired or wireless connection. The monitoring system 122 may be implemented in a cloud computing environment 120 or other network environment. The data acquisition component 104 may therefore be configured to communicate with the cloud network 120 for transmission of the sensor data to the monitoring system 122. As explained in more detail below, the monitoring system 122 may process and provide the received data to one or more computing system for display on one or more display devices. In this manner, the data acquisition component 104 may provide the measured data of the monitored site 102 for analysis by a site monitor or administrator.

Figure 3:
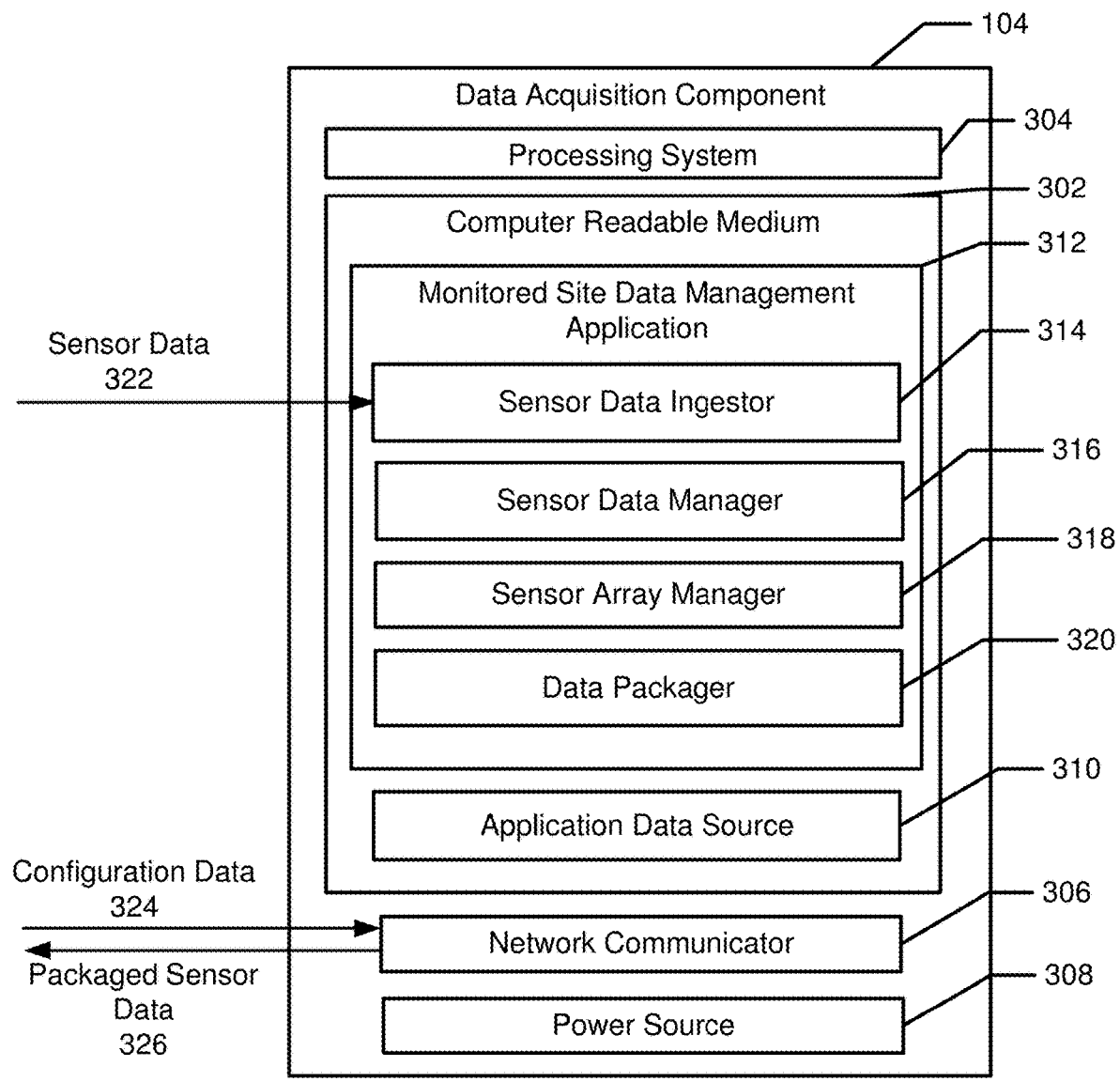
FIG. 3 is a schematic diagram illustrating a sensor array management system for collecting, managing, and transmitting sensor data received from a sensor array.

FIG. 3 is a schematic diagram illustrating the data acquisition component 104 for collecting, managing, and transmitting sensor data received from a sensor array 103 described above. In some instances, a monitored site data management application 312 may be executed on the data acquisition component 104 to perform one or more of the operations described herein. The monitored site data management application 312 may be stored in a computer readable media 302 (e.g., memory) and executed on a processing system 304 of the data acquisition component 104 or other type of computing system, such as that described below. For example, the monitored site data management application 312 may include instructions that may be executed in an operating system environment, such as a Microsoft Windows™ operating system, a Linux operating system, or a UNIX operating system environment. The computer readable medium 302 includes volatile media, nonvolatile media, removable media, non-removable media, and/or another available medium. By way of example and not limitation, non-transitory computer readable medium 302 comprises computer storage media, such as non-transient storage memory, volatile media, nonvolatile media, removable media, and/or non-removable media implemented in a method or technology for storage of information, such as computer readable instructions, data structures, program modules, or other data.

According to one instance, the data acquisition component 104 may also include a network communicator 306 for communicating with the network 120 and/or the monitoring system 122. In one example, the network communicator 306 may include wireless communication devices for transmitting a wireless communication signal to the network 120. The network communicator 306 may utilize any known or hereafter developed wireless communication protocol, such as cellular, satellite, Bluetooth, WiFi, or any other wireless system. The network communicator 306 may therefore include many types of transmitters, such as antennas, directional antennas, satellite dishes, and the like. The data acquisition component 104 may also include a power source to provide operational power to the components of the data acquisition component 104. In some instances, the power source 308 may include batteries, solar cells, one or more plugs for connection to a power grid, and the like. The network communicator 306 and/or the power source 308 may also be configured to provide status information or data to the monitored site data management application 312. Such information may be transmitted to the monitoring system 122 as operational status information of the data acquisition component 104.

The data management application 312 may utilize an application data source 310 of the computer readable media 302 for storage of data and information associated with the data acquisition component 104. For example, the data management application 312 may store information associated with the sensor array 103 and/or the monitored site in general, including data and information received from the multiple sensors 112 of the data array 103, information unique to the monitored site 102 (such as an identifier of the monitored site 102, address information of sensors 112 of the sensor array 103, and operational status information of the components of the data acquisition component 104 and/or the sensors 112 of the sensor array 103), and the like. In general, any data or information utilized by the data management application 312 may be stored and/or retrieved via the data source 308.

The data management application 312 may include several modules or programs to perform one or more of the operations described herein. For example, a sensor data ingestor 314 may be included in the data management application 312 to receive data and information 322 from one or more sensors 112 of the sensor array 103. For example, sensor data 322 may be transmitted from the sensors 112 of the sensor array 103 via the communication wires 110 of the conduit 108 to the sensor data ingestor 314. The sensor data ingestor 314 may store the received sensor data 322 in the application data source 310, in some instances. Further, the data management application 312 may include a sensor data manager 316 configured to process the received sensor data 322. In one example, packets of the received sensor data 322 may be addressed with a corresponding sensor identifier to indicate which sensor of the array 103 provides the sensor information. The sensor data manager 316 may extract or analyze the address associated with a packet of data of the sensor data 322 to determine which sensor transmits the data packet. The sensor data manager 316 may also associate the sensor identifier in the application data source with the corresponding sensor data. In the instance where the sensor array 103 includes multiple communication wires 110, the sensor data manager 316 may determine the communication wire from which information or data is received and store the sensor data 322 with an indication of the sensor group from which the sensor data 322 was received. In general, the sensor data manager 316 organizes the received sensor data 322 based on sensor location within the sensor array 103 and the monitored site 102 for use by the monitoring system 122, as is discussed in more detail below.

The data management application 312 may also include a sensor array manager 318 configured to manage operational states of the sensor array. For example, the sensor array manager 318 may generate and assign unique addresses to the various sensors 112 of the sensor array 103. The sensor array manager 318 may also receive data or information from the sensors 112 of the array 103 that indicate an operational status of the sensors and, in response to the received information, store the operational status of the sensors 112 in the application data source 310. The sensor data manager 318 may communicate with the sensor array manager 318 to determine the particular sensors 112 of the array 103 from which sensor data 322 is received.

In another example, sensor array manager 318 and/or sensor data manager 316 may control aspects of the sensor data 322 collection. For example, sensors 112 of the sensor array 103 may obtain sensor measurements or readings in response to a request or activation signal transmitted to the sensors 112 via the communication wire 110. In this manner, the communication wire 110 may be bi-directional to provide both upstream and downstream communications. The commands or requests to obtain a measurement and provide said measurement to the data acquisition component 104 may be addressed in a similar manner as described above such that particular sensors 112 may receive the request. In some instances, the sensor data manager 316 and/or the sensor array manager 318 may be configured to determine a time to request site measurements from the sensors 112, generate the requests, and transmit the requests on the communication wire 110. The request for sensor data 322 may occur at a regular frequency, such as every 30 minutes, every hour, every day, etc. The frequency at which requests for sensor information 322 is requested may be provided by the monitoring system 122, as described in more detail below. In another example, the data management application 312 may include artificial intelligence processes to determine the frequency of data collection and adjust the sensor data manager 316 and/or sensor array manager 318 accordingly.

A data packager 320 may also be included in the data management application 312. The data packager 320 may be configured to receive the sensor data 322 from the sensor data manager 316 or from the application data source 310 and package the sensor data 322 for transmission to the monitoring system 122. Packaging the sensor data 322 may include collecting data from the same sensor into a package, addressing data packets with an address associated with the monitoring system 122, discarding erroneous sensor data 322, collecting sensor data based on date/time of collection, and the like. The data packager 320 (or other component of the data management application 312) may utilize the network communicator 306 for transmitting the packaged sensor data 326 to the monitoring system 122. As such, the data packager 320 may generally prepare the sensor data 322 and/or sensor array information for transmission to the monitoring system 122 via the network communicator 306.

In addition, the network communicator 306 may receive sensor array configuration data 324 from the monitoring system 122 or from another computing device. Thus, the data management application may be accessible through a wired or wireless communication for providing the configuration data 324. The sensor array manager 318 may utilize the configuration data 324 to configure one or more aspects of the sensor array 103. For example, the sensor array manager 318 may adjust the frequency at which sensor data 322 is requested or stored in response to the configuration data 324. In another example, the addressing scheme utilized by the sensor array 103 may be configured to include more or fewer sensors 112 based on the configuration data 324. Other aspects of the data management application 312 may also be configured or altered based on the configuration data 324. In this manner, the sensor array 103 deployed at the monitoring site 102 may be remotely configured via the configuration data 324 transmitted to the data acquisition component 104.

It should be appreciated that the components described herein are provided only as examples, and that the application 312 may have different components or programs, additional components or programs, or fewer components or programs than those described herein. For example, one or more components or programs as described in FIG. 3 may be combined into a single component or program. As another example, certain components or programs described herein may be encoded on, and executed on other computing systems, such as on one remotely coupled to the data acquisition component 104.

Through the sensor array 103 described herein, conditions at a monitored site 102 may be determined remotely. Further, the measurements of conditions at the monitored site 102 may be processed by a monitoring system 122 for display to a remotely located monitoring party. Continuous, real-time monitoring of temperature, water levels, and ORP of a monitored site 102 provides advantages for monitoring the site over other types of site measurements. In particular, the display and consideration of a combination of measured temperature, water levels, and ORP of the subsurface conditions of the monitored site 102 provides a beneficial snapshot of the conditions of the site 102.

As mentioned above, the monitoring system 122 may receive sensor data 322 from a data acquisition component 104 of a sensor array 103 deployed at a monitored site 102. In some instances, the monitoring system 122 may process the received sensor data 322 and provide a dashboard or other user interface through which the sensor data 322 may be displayed or viewed by a user of the monitoring system 122. More particularly, a user may utilize a computing device 124, such as a smart phone, laptop computer, desktop computer, or any other computing device 124 configured to communicate with cloud network 120, to access the monitoring system 122 and view the sensor data 322 obtained by the sensor array 103. In one instance, the computing device 124 may execute a user interface 126 to provide access to the monitoring system 122 and the sensor data 322 managed by the monitoring system 122. In this manner, a user of the computing device 124 may monitor the conditions of the monitored site 102 remotely via the monitoring system 122, removing the need to visit the monitored site 102 to collect the subsurface samples. In addition, the monitoring system 122 may combine, alter, or otherwise process the sensor data 322 for display via the user interface 126 for ease of understanding by the user of the computing device 124.

Figure 4:
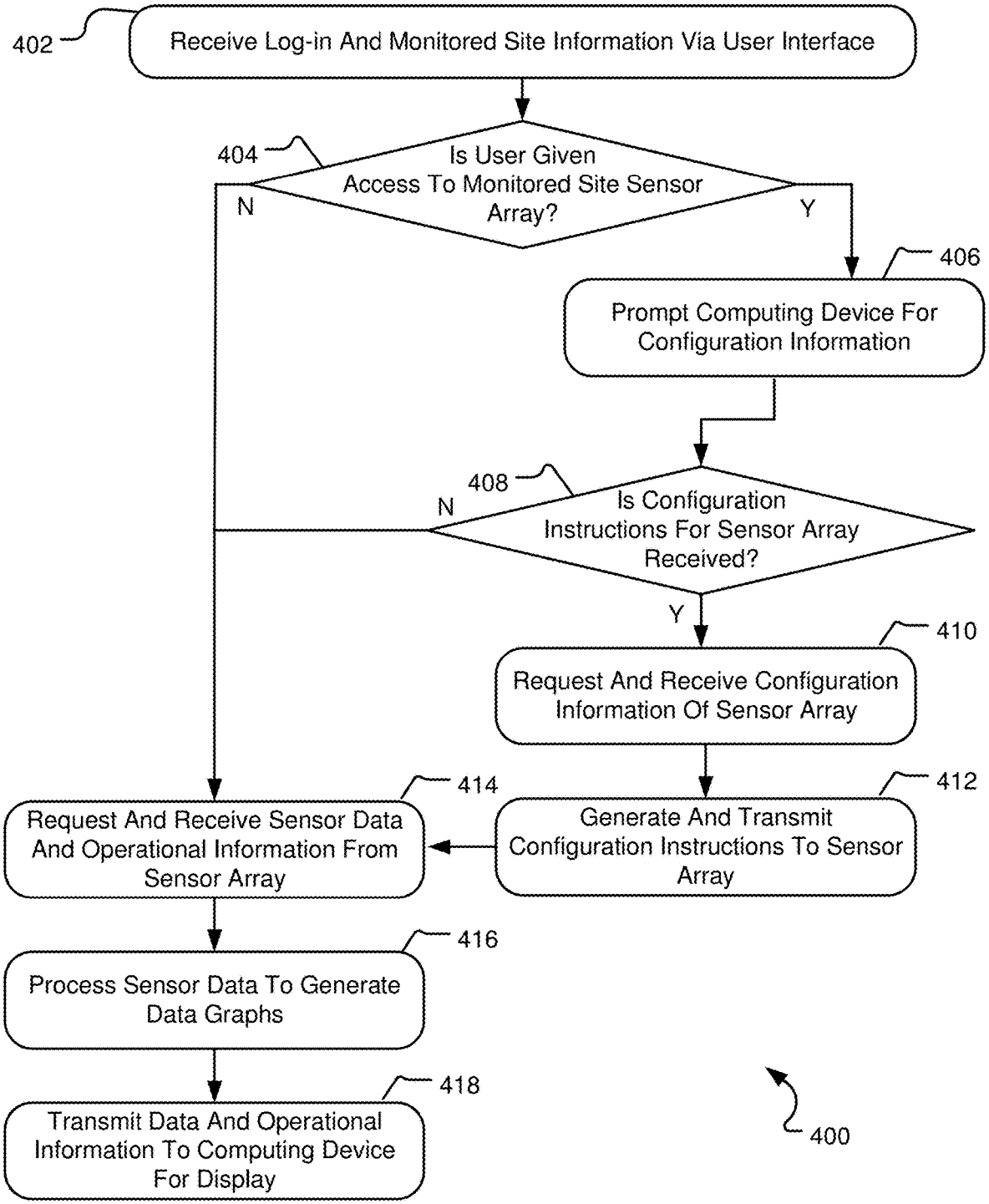
FIG. 4 is a flowchart of a method for a monitoring system to collect measurements of a monitored site and provide the measurements to a requesting device.

FIG. 4 is a flowchart of a method 400 for the monitoring system 122 to collect measurements of a monitored site 102 and provide the measurements to the computing device 124. In some instances, the operations of the method 400 may be performed by the monitoring system 122 through one or more software programs, one or more hardware components, or a combination of hardware and software components. In addition, one or more of the operations of the method 400 may be performed by other components or devices, such as the computing device 124 or user interface 126 of FIG. 1B. Through the method 400, the monitoring system 122 may provide sensor data 322 from the sensor array 103 to the user interface 126 of the computing device 124 for display. In addition, the computing device 124 may provide configuration instructions for configuring the operation of the sensor array 103 to initiate, alter, or control the collection of sensor data 322 at the monitored site 102.

Beginning in operation 402, the monitoring system 122 may receive log-in credentials and monitored site 102 identification information via the user interface 126 of the computing device 124. In one example, the user interface 126 may include a browser program executed on the computing device 124 to connect to the monitoring system 122 and receive data/information from the monitoring system 122. Other programs configured to access and communicate with the cloud network 120 and/or the monitoring system 122 may also be executed by the computing device 124 to provide the log-in credentials and monitored site 102 identification information to the monitoring system 122.

Figure 5:
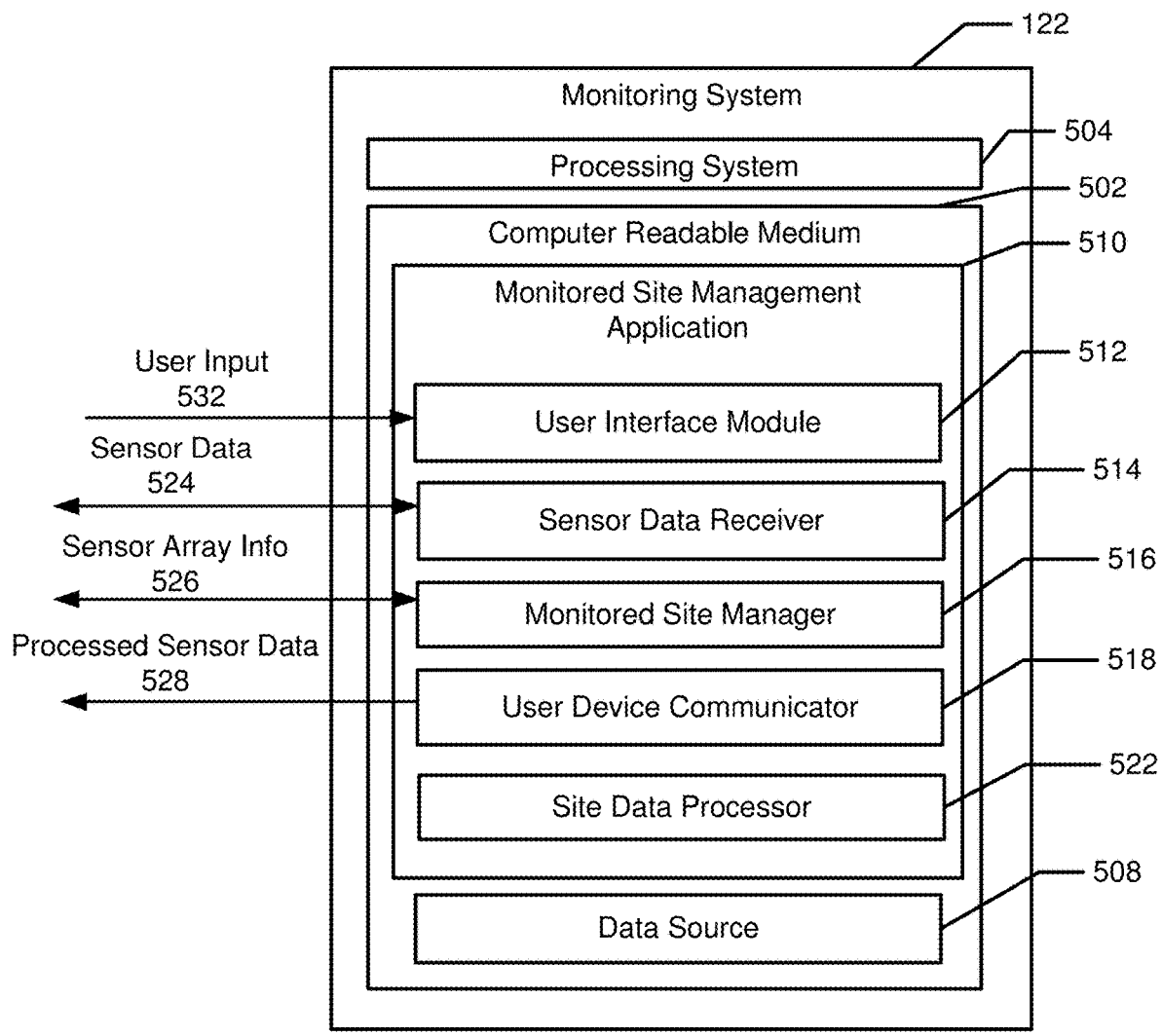
FIG. 5 is a schematic diagram illustrating a monitoring system for collecting, managing, and displaying sensor data received from a sensor array deployed at a monitoring site.

The monitoring system 122 may include components and procedures to communicate and receive information from the user interface 126 of the computing device 124. For example, FIG. 5 is a schematic diagram 500 illustrating the monitoring system 122 for collecting, managing, and displaying sensor data 322 received from a sensor array 103 deployed at a monitoring site 102. A monitored site management application 510 may be executed by the monitoring system 122 to perform one or more of the operations described in the method 400 of FIG. 4. As such, the monitored site management application 510 may be stored in a computer readable media 502 (e.g., memory) and executed on a processing system 504 of the monitoring system 122 or other type of computing system. Similar to above, the computer readable medium 502 includes volatile media, nonvolatile media, removable media, non-removable media, and/or another available medium.

According to one embodiment, the monitoring system 122 may communicate with the computing device 124 via a user interface module 512. For example, user interface module 512 may communicate with user interface 126 of computing device 124 to receive log-in credentials and monitored site 102 identification information via the user interface 126 of the computing device 124. The user interface module 512 may, in some instances, process the received user inputs 532 from the user interface 126 to perform various functions. For example, the user interface module 512 may compare the log-in credential information from the user interface 126 to determine a level of access to information associated with the monitored site 102. The log-in information may include a username and password combination that is utilized to identify the computing device 124 requesting access to the monitored site information. The monitored site management application 510 may utilize a data source 508 of the computer readable media 502 for storage of data and information associated with the monitoring system 122. For example, the monitored site management application 510 may store information associated with user interface 124 access to sensor data received from monitored sites 102, sensor data 524 received from one or more sensor arrays, processed sensor data for display via a user interface 124, and the like. In general, any data or information utilized by the monitored site management application 510 may be stored and/or retrieved via the data source 508.

To determine a level of access to the requesting computing device 124, the user interface module 512 may compare the received user input 532 to information stored in the data source 508 to identify the requesting device and determine a level of access to the stored data. In some instances, the stored monitored site data 524 may be available to general users or may be restricted to particular users of the monitoring system 122. Variations in the level of access may therefore be based on the credential information provided by the computing device 124. Further, the level of access may vary based on the monitored site 102 identified in the user input 532. For example, a first monitored site may provide access to all sensor data 524 to all users associated with the monitoring system 122 while a second monitored site may restrict access to sensor data 524 to particular requesting devices. In this manner, the user interface module 512 may compare the received log-in credentials and/or monitored site identifier to determine a level of access for the requesting device 124.

Returning to FIG. 4, the monitoring system 122 determines if the user is granted access to configure the monitored site sensor array 103 in operation 404. As mentioned above, the monitoring system 122 may grant levels of access to computing devices 124 and/or user interface 126 for interacting with sensor data 524 received from a monitored site 102. In some instances, the level of access may include configuring one or more aspects of the sensor array 103 at the monitored site 102, such as configuring an addressing scheme of the array, altering or setting a frequency of data acquisition, activating or deactivating one or more sensors of the sensor array 103, and the like. If the monitoring system 122 determines that the computing device 124 has access to configure the sensor array 103 of the monitored site 102 based on information stored in the data source 508, the monitoring system may prompt the computing device 124 for the sensor array configuration information in operation 406. The configuration information may be provided via the user interface 126 and transmitted to the user interface module 512 as described above.

In operation 408, the monitoring system 122 may determine if sensor array configuration information is received via the user interface 126 in operation 408. In some instances, the computing device 124 may not configure the sensor array 103 as the operational status of the sensor array is in a preferred state. If configuration instructions are received, the monitoring system 122 may request and receive configuration information of the sensor array 103 from the data acquisition module 106 of the array in operation 410. In particular and returning to FIG. 5, the monitored site management application 510 may include a monitored site manager 516 for communicating with the sensor array 103 at the monitored site and configuring the sensor array. The monitored site manager 516 may thus generate and transmit one or more instructions to the network communicator 306 of the data acquisition component 106 of the sensor array 103. One type of instructions may include a request to receive configuration status information 526 of the sensor array 103 from the data acquisition component. In response, the data acquisition component 106 may generate one or more packets of configuration status information 526 of the sensor array 103 and transmit, utilizing the network communicator 306, the status information to the monitoring system 122.

The monitored site manager 516 may receive the configuration status information 526 of the sensor array 103. The configuration status information 526 of the sensor array 103 may be stored in the data source 508 for use by the monitoring system 122. In operation 412, the monitored site manager 516 may, based on a current configuration and/or configuration status of the sensor array 103, generate one or more instructions for configuring the sensor array 103 according to the received configuration information from the computing device 124. For example, the current configuration of the sensor array 103 may match the requested configuration identified in the configuration information from the computer device 124 such that no additional instructions for configuring the sensor array 103 is needed. In another example, the configuration information of the array 103 may indicate a data acquisition frequency of the sensors 112 of the sensor array 103. However, the request to configure the sensor array 103 may include a different acquisition frequency. In response to the configuration instructions from the computing device 124, the monitored site manager 516 may generate one or more instructions for transmission to and execution by the data acquisition component 106 of the sensor array to reconfigure the sensor array according to the configuration instructions.

In some instances, the computing device 124 does not configure the sensor array, either because the computing device 124 is not granted such access to the sensor array or configuration instructions are not received from the computing device 124. Further, in some instances, configuration information of the sensor array 103 may be requested and received by the monitoring system 122 at any time. For example, the monitored site manager 516 may be configured to maintain operation of the sensor array 103 absent instructions from a computing device 124. In this example, the monitored site manager 516 may periodically request and receive operational status information of the sensor array 103 and alter the configuration in response to one or more aspects of the configuration, such as an alarm condition, a detected fault of a component, or in response to a request from the data acquisition component 106 of the array 103.

Regardless of the configuration of the sensor array 103, the monitoring system 122 may request and receive sensor data 524 in operation 414 of method 400. In particular, a sensor data receiver 514 may request and receive the sensor data 524 from the data acquisition component 106, as discussed above. In some instances, the sensor data 524 may be pushed to the monitoring system 122 by the sensor array 103 when measured, at a regular interval, upon receiving a request, or in response to any other input. In another example, the monitoring system 122 may receive a request for the sensor data 524 of a particular monitored site 102 from a user interface 126 of a computing device 124 and, in response, request the data from the sensor array 103 associated or deployed at the monitored site 102. The sensor data receiver 514 of the monitored site management application 510 may receive the requested sensor data 524. In addition, the monitored site manager 516 may request and receive operational information 526 of the sensor array 103 in operation 414. As discussed in more detail below, the operational information of the sensor array 103 may be packaged and provided to the user interface 126 of the computing device 124.

In operation 416, the sensor data 524 and/or operational information 526 received from the sensor array 103 may be processed by the monitored site management application 510 for display on the user interface 126 of the computing device 124. In particular, the monitored site management application 510 may include a site data processor 522 for processing the received data. Processing of the site data may include combining data and information for display in one or more graphs or displays, as discussed in more detail below with reference to FIGS. 6-9. The site data processor 522 may also package the received data for transmission to the computing device 124 and display in the user interface 126 executed by the computing device. Additional processing of the site data may also be performed to generate the graphs, displays, operational data listings, sensor array configurations, and the like available via the user interface 126. In general, any data, visual, or information provided in the user interface 126 may be generated by the site data processor 522.

In some instances, the monitored site management application 510 may utilize machine learning algorithms or other artificial intelligence algorithms to process the received data. For example, the monitored site management application 510 may receive vast amounts of data from multiple monitored sites and, through a machine learning process, determine conditions of the monitored sites that may lead to particular outcomes. This understanding of the received data may inform the management application 510 of potentially harmful conditions of the monitored site 102 and appropriate warnings or information may be provided to the computing device 124 for display. Other conclusions of the received data may be generated through other machine learning processes to provide the monitored site management application 510 with a conclusion based on the received data.

In operation 418, the monitored site management application 510 may transmit the sensor data 524 and/or operational information 526 to the computing device 124 for display in the user interface 126. For example, the monitored site management application 510 may include a user device communicator 518 configured to transmit the processed sensor data 528 and/or operational information or otherwise communicate with the computing device 124. The processed sensor data 528 may be displayed via the user interface 126 of the computing device 124 to a user of the computing device to obtain an understanding of the conditions of the monitored site 102 as measured by the sensors 112 of the sensor array 103 deployed at the monitored site.

As mentioned above, the monitored site management application 510 may process the sensor data 524 received from the sensor array 103 for display in the user interface 126. The user interface 126 may include various graphs and other visuals for displaying the sensor data 524 provided by the monitored site management application 510. In one example, the user interface 126 may include a highlight panel that provides a selected group of measurement data for presentation in a single interface, including notification for parameters that are close to or exceeding set alarm levels. In another example, the raw measurement data may be graphed and presented in separate visuals for more detailed information of the measurements of the monitored site 102.

Figure 6:
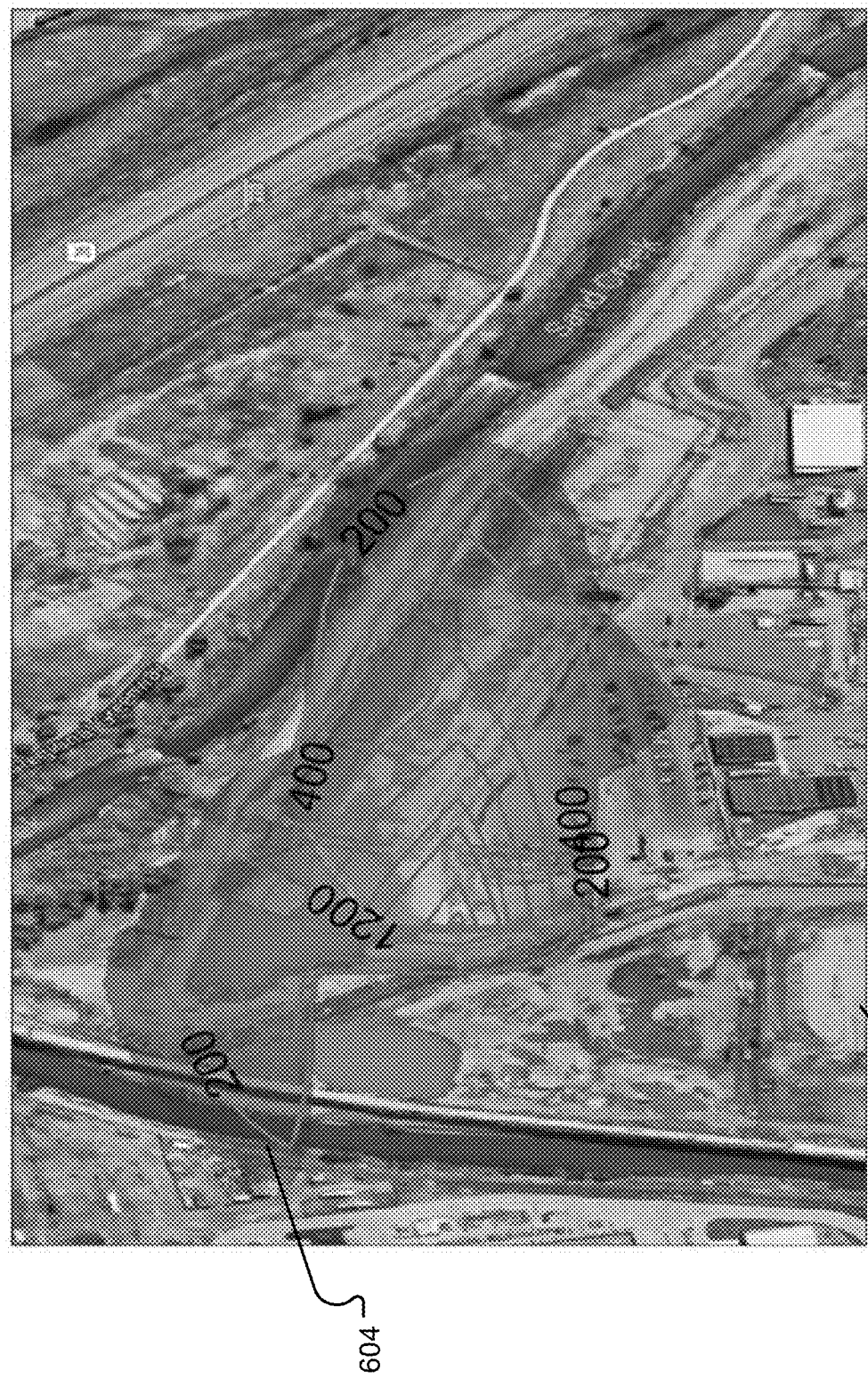
FIG. 6 is an example screenshot of a user interface displaying a contoured natural source zone rate at a monitored site.

Further still, processing of the sensor data 524 may be performed and displayed. In one example, a time series of contoured natural source zone (NSZD) rates may be determined and displayed. FIG. 6 is an example screenshot 600 of a user interface displaying a contoured natural source zone rate at a monitored site 102. The NSZD graph 600 may include, in some instances, a map or aerial photograph 602 of the monitored site 102 associated with the sensor data 524 being displayed. A time series of contoured NSZD rates 604 of the monitored site 102 as measured via the sensors 112 of the sensor array 103 may also be displayed. In one instance, the contoured NSZD rates may be obtained utilizing a single-stick for reducing temperature data to NSZD rates. Temperature data obtained via the sensor array 103 for a monitored site 102 may be processed by the monitoring system 122 to generate one or more contoured NSZD maps correlated to a map of the monitored site 102. In one instance, the monitoring system 122 may receive, from the sensor array 103, geographical information of the monitored site (such as latitude and longitude degrees of the monitored site 102) and location information for the temperature sensors 112b of the sensor array 103. With this information, the monitoring system 122 may correlate particular temperature measurements of the monitored site 102 to a latitude and longitude location. This temperature data may be collected and mapped to generate the contoured NSZD rate for the monitored site 102. In addition, the processed information may be transmitted to the computing device 124 for display in the user interface 126, as shown in the screenshot 600 of FIG. 6. In another instance, a time series of contoured maximum true and background-corrected temperatures may similarly be illustrated in the user interface 126 of the computing device 124.

Figure 7:
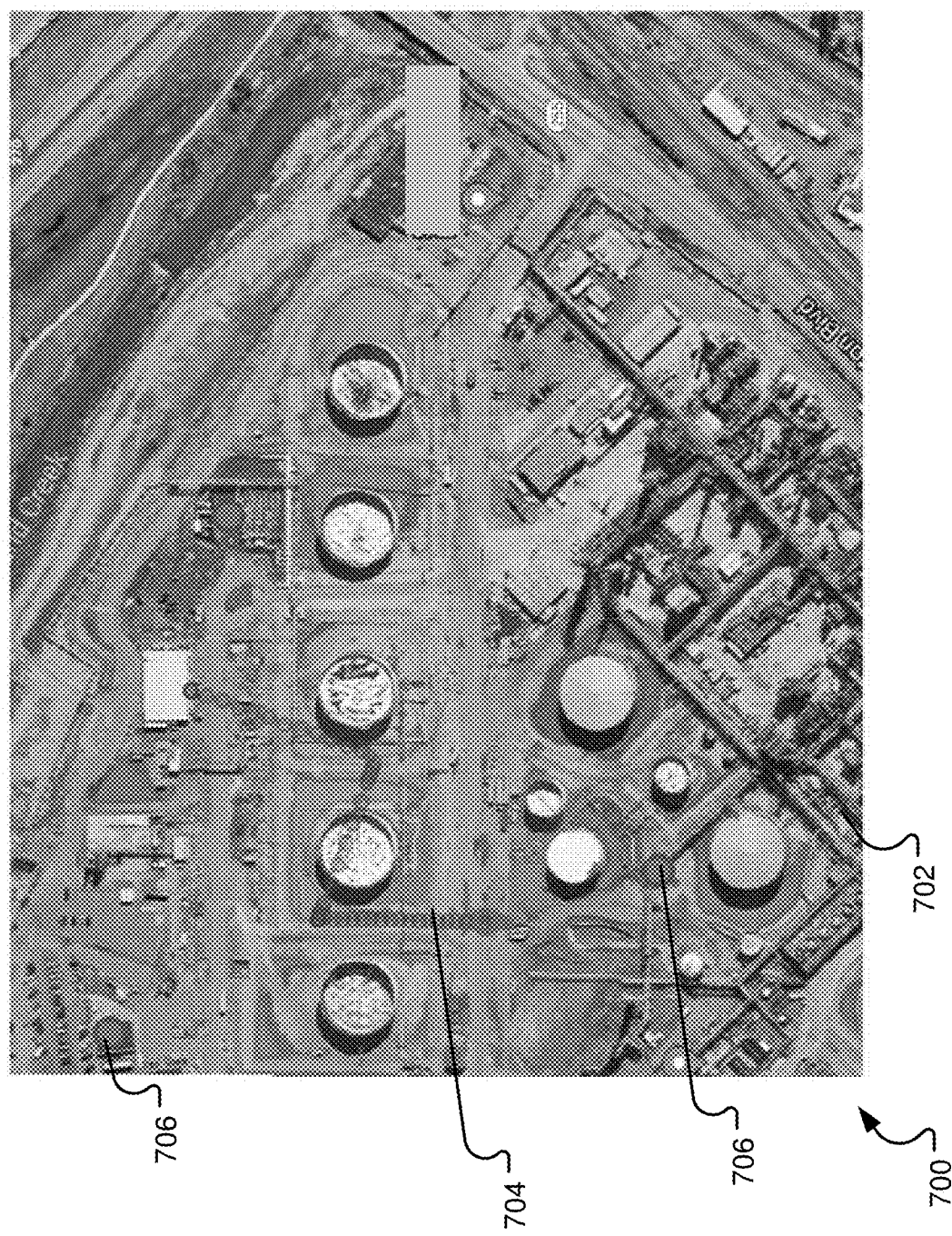
FIG. 7 is an example screenshot of a user interface displaying a simulated groundwater flow at a monitored site.

In another example, simulated groundwater flow directions may be mapped over a site map or aerial photograph based on the water level measurements obtained by the sensor array 103 at a monitored site 102. For example, FIG. 7 is an example screenshot 700 of the user interface 124 displaying a simulated groundwater flow at a monitored site 102. As shown in the screenshot 700, groundwater flow graph 700 may include, in some instances, a map or aerial photograph 702 of the monitored site 102 associated with the sensor data 524 being displayed. Estimated locations of monitor wells 706 or other placement of the sensors 112 of the sensor array 103 may also be illustrated in the screenshot 700. Estimated groundwater flow paths 704 (particle trails) for fixed time periods (such as 10 days, 100 days, 1000 days, etc.) posted either at the center or corners of water-level sets defining a head surface in plain-view or cross-section may also be illustrated. Periodic temporal groundwater flow vectors may be sequentially connected head to tail to form temporal groundwater flow trails 704. In some instances, the flow vectors combined to form the illustrated flow trail 704 may be determined by the monitoring system 122 in response to water-level measurements of the sensor array 103. In one instance, flow vectors may include estimates of the uncertainty of the flow direction based on uncertainties in input parameters including water levels, retardations, and declining concentrations due to reactions. Temporal sequences of groundwater flow trails may then be sequentially presented to illustrate groundwater flow 704 through the fixed time period.

ORP measurements may also be presented in the user interface 126 of the computing device 124. For example, a time series of contoured select ORP values (such as ORP minimums) may be mapped onto a site map, an aerial photograph, or in a cross-section map, in a similar manner as described above with relation to the screenshot 600 of FIG. 6. In particular, the monitoring system 122 may receive ORP measurements of the monitored site 102 from the sensor array 103 and process the ORP measurements over a period of time to obtain the time series of contoured ORP values. The ORP values may be correlated along vertical or horizontal planes through the time period. Further, the monitoring system 122 may determine estimates of aqueous contaminant concentrations of critical constituents based on thermodynamics. For example, given:

$$pe + pH = -0.5 \log[H_2]$$

$$[H_2] = -10^{2(pe+pH)}$$

For an Ag—AgCL reference electrode $$pe \cong (ORP + 200)/59.2$$

Figure 8A:
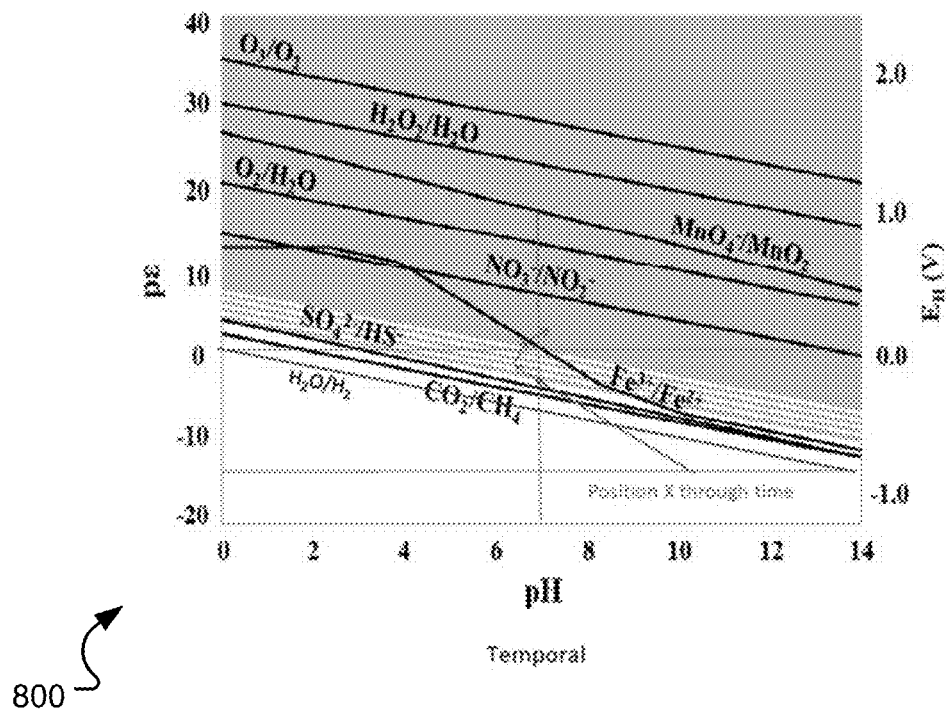
FIGS. 8A and 8B are example screenshots of a user interface displaying ORP values on a pe-pH stability field of a monitored site.
Figure 8B:
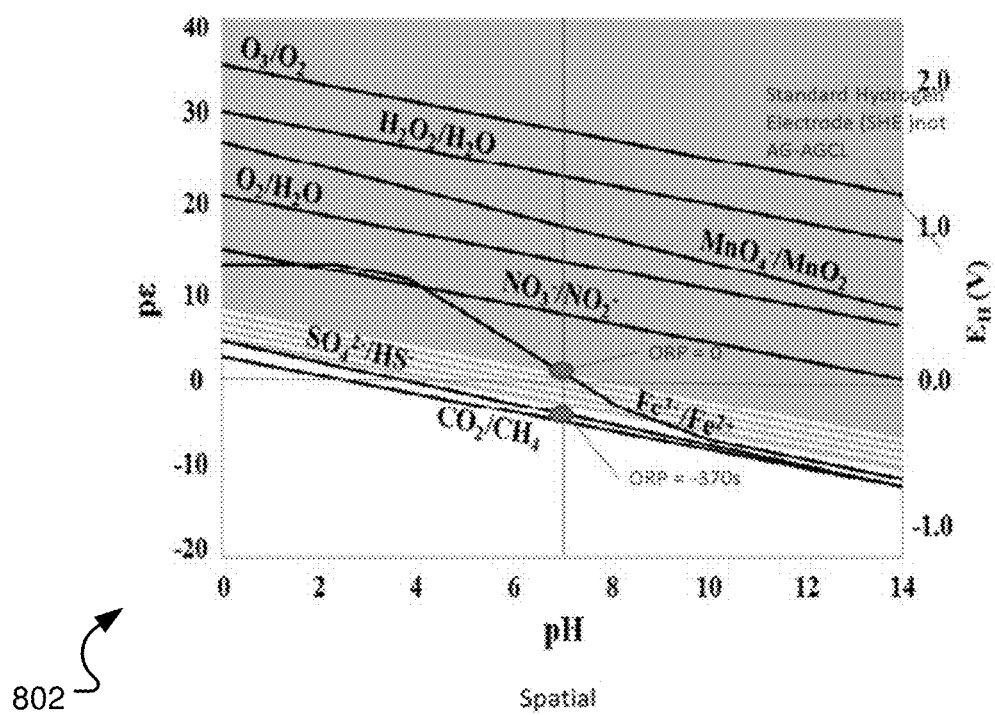

These estimated aqueous contaminant concentrations of critical constituents may be based on correlations between observed concentrations for redox parameters and pe/pH. As shown in FIG. 8A, the monitoring system 122 may display a temporal graph of the estimated aqueous contaminant concentrations of critical constituents 800 and/or a spatial graph of the estimated aqueous contaminant concentrations of critical constituents 802. In particular, the user interface 126 may display critical ORP values on a pe-pH stability field with lines eqilibria for key solids and/or aqueous phase constituents. Presentation of the ORP data may be measured pH values or assumed pH values.

Figure 9:
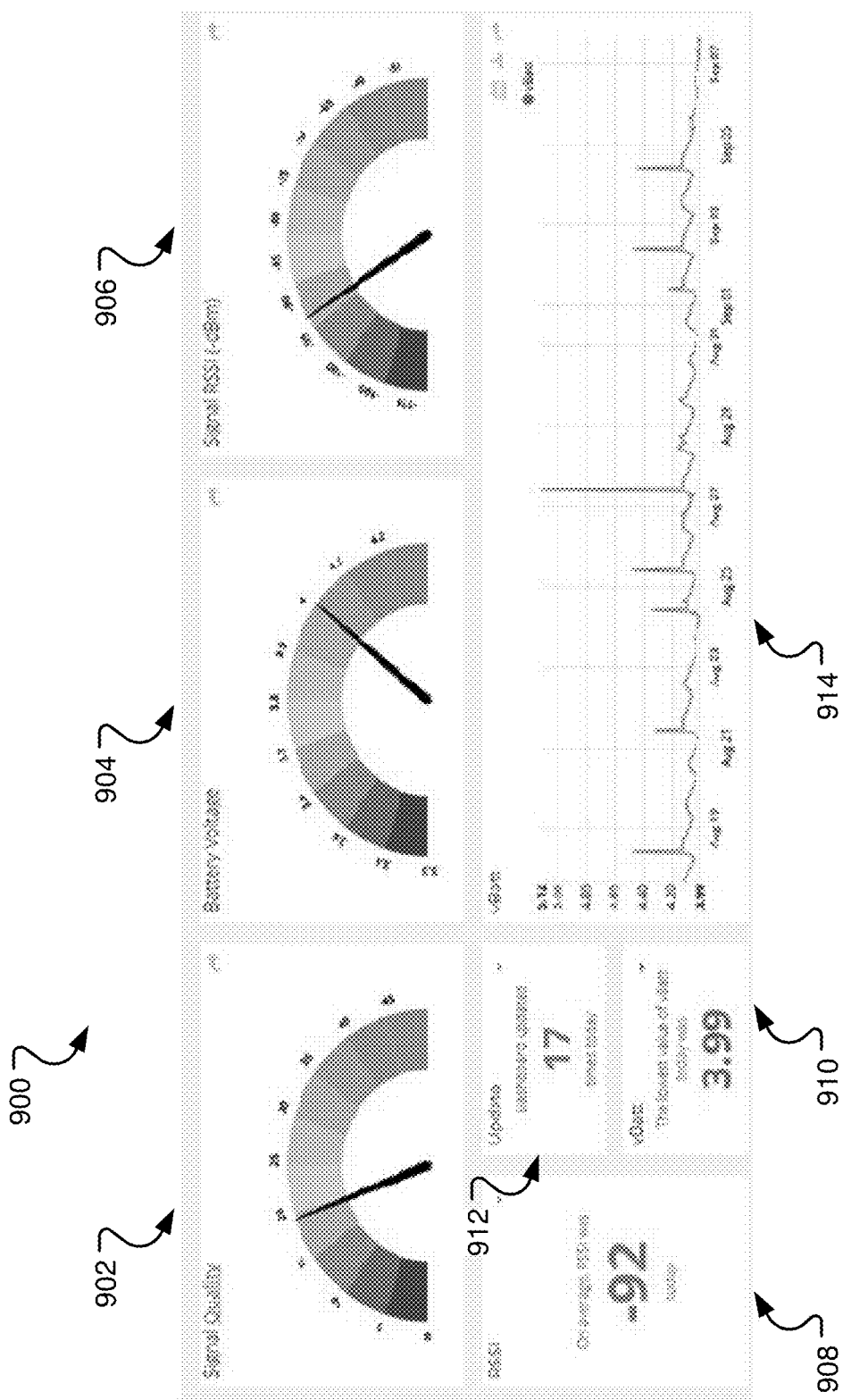
FIG. 9 is an example screenshot of a user interface displaying a sensor array hardware status panel of a sensor array deployed at a monitored site.

In addition to the sensor data 524 received from the sensor array 103, the monitoring system 122 may also process and provide sensor array configuration and/or operational information in the user interface 126. For example, FIG. 9 is an example screenshot of a user interface 124 displaying a sensor array hardware status panel 900 of a sensor array 103 deployed at a monitored site 102. The status panel 900 may include information associated with the operation of the sensor array 103 of the monitored site 102 as provided to the monitoring system 122 from the data acquisition component 106 of the array. Although illustrated as providing particular information, the status panel 900 may include more or less operational information and may, in some instances, be configurable via the user interface 126 to alter the display of the information. Through the status panel 900, a user of the user interface 126 may determine an operational condition of the status array 103 to monitor for faults or other operational issues of the array 103.

In the example illustrated in FIG. 9, the status panel 900 may include one or more panels associated with a wireless signal transmitted by the sensor array 103 and/or one or more panels associated with the power source 308 of the array 103. Other panels may also be included, such as panels illustrating an operational condition of one or more of the sensors 112 of the sensor array 103, including status of reference electrodes of ORP sensors. The information may be presented in a series of panels including a visual indicator 902-906, such as a color-coded range of corresponding values. The visual indicators 902-906 may include a portion corresponding to an alarm condition for the operational parameter of the array 103 to indicate within the user interface 126 a potential alarm condition of the array. The status panel 900 of FIG. 9 includes a wireless signal quality indicator 902, a wireless signal Received Signal Strength Indicator (RSSI) 904, and a battery voltage indicator 904. In addition to visual indicators, the status panel 900 may include panels providing the measured operational values, such as a RSSI value panel 908, a battery voltage panel 910, and/or a upload panel 912 indicating the number of information uploads to the monitoring system 122 from the sensor array 103 for the particular day being viewed. In addition, a voltage battery graph 914 may be presented illustrating battery voltages measured over a time period, such as over the previous week, previous month, previous 24 hours, and the like. The information of the status panel 900 may therefore provide a user of the user interface 126 with information on the status of the sensor array 103 for the particular monitored site 102 for maintenance of the sensor array.

Figure 10:
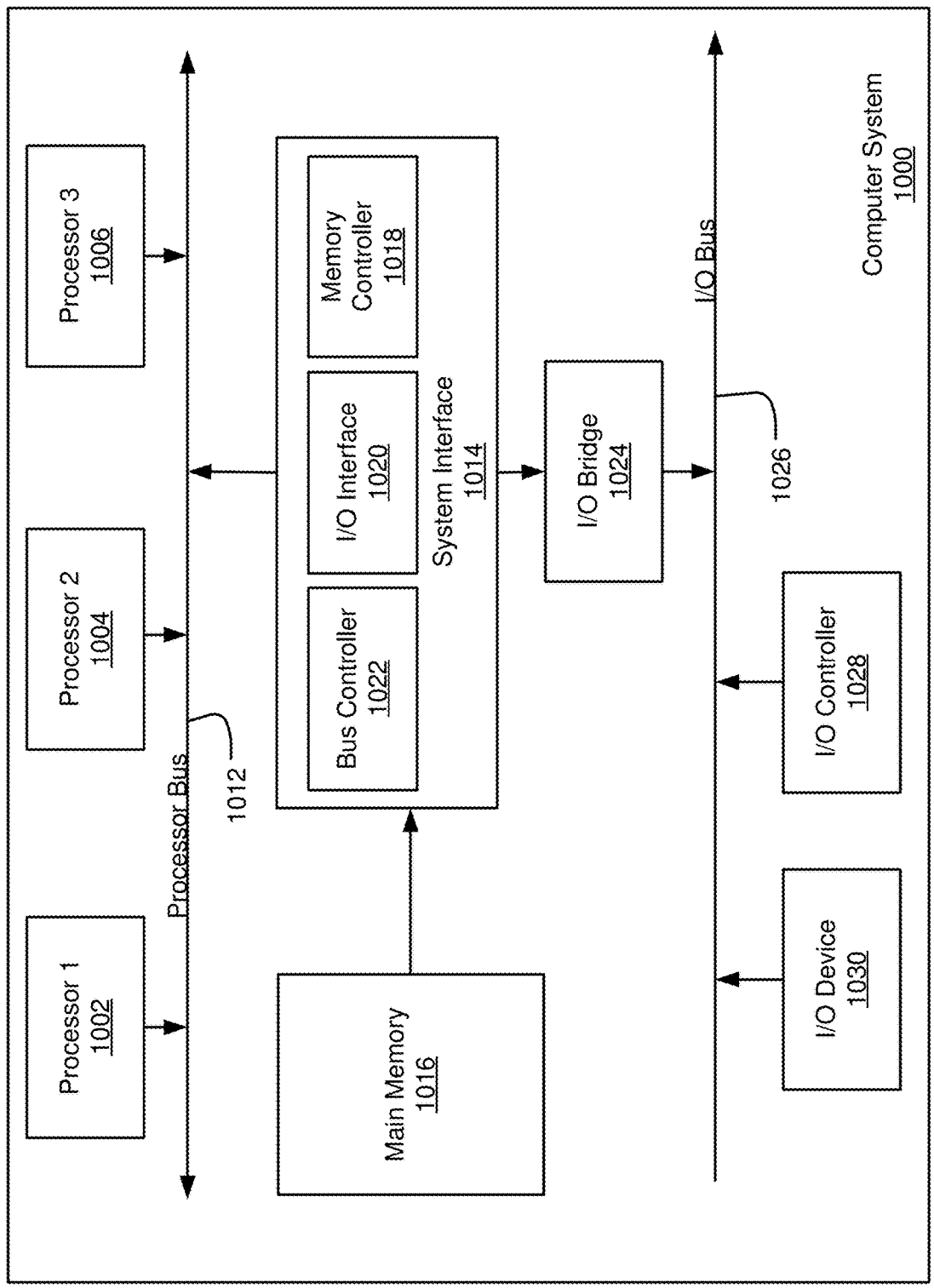
FIG. 10 is a diagram illustrating an example of a computing system which may be used in implementing embodiments of the present disclosure.

FIG. 10 is a block diagram illustrating an example of a computing device or computer system 1000 which may be used in implementing the embodiments of the subsurface monitoring devices disclosed above. For example, the computing system 1000 of FIG. 10 may be the monitoring system 122 discussed above. The computer system (system) includes one or more processors 1002-1006. Processors 1002-1006 may include one or more internal levels of cache (not shown) and a bus controller or bus interface unit to direct interaction with the processor bus 1012. Processor bus 1012, also known as the host bus or the front side bus, may be used to couple the processors 1002-1006 with the system interface 1014. System interface 1014 may be connected to the processor bus 1012 to interface other components of the system 1000 with the processor bus 1012. For example, system interface 1014 may include a memory controller 1014 for interfacing a main memory 1016 with the processor bus 1012. The main memory 1016 typically includes one or more memory cards and a control circuit (not shown). System interface 1014 may also include an input/output (I/O) interface 1020 to interface one or more I/O bridges or I/O devices with the processor bus 1012. One or more I/O controllers and/or I/O devices may be connected with the I/O bus 1026, such as I/O controller 1028 and I/O device 1030, as illustrated.

I/O device 1030 may also include an input device (not shown), such as an alphanumeric input device, including alphanumeric and other keys for communicating information and/or command selections to the processors 1002-1006. Another type of user input device includes cursor control, such as a mouse, a trackball, or cursor direction keys for communicating direction information and command selections to the processors 1002-1006 and for controlling cursor movement on the display device.

System 1000 may include a dynamic storage device, referred to as main memory 1016, or a random access memory (RAM) or other computer-readable devices coupled to the processor bus 1012 for storing information and instructions to be executed by the processors 1002-1006. Main memory 1016 also may be used for storing temporary variables or other intermediate information during execution of instructions by the processors 1002-1006. System 1000 may include a read only memory (ROM) and/or other static storage device coupled to the processor bus 1012 for storing static information and instructions for the processors 1002-1006. The system set forth in FIG. 10 is but one possible example of a computer system that may employ or be configured in accordance with aspects of the present disclosure.

According to one embodiment, the above techniques may be performed by computer system 1000 in response to processor 1004 executing one or more sequences of one or more instructions contained in main memory 1016. These instructions may be read into main memory 1016 from another machine-readable medium, such as a storage device. Execution of the sequences of instructions contained in main memory 1016 may cause processors 1002-1006 to perform the process steps described herein. In alternative embodiments, circuitry may be used in place of or in combination with the software instructions. Thus, embodiments of the present disclosure may include both hardware and software components.

A machine readable medium includes any mechanism for storing or transmitting information in a form (e.g., software, processing application) readable by a machine (e.g., a computer). Such media may take the form of, but is not limited to, non-volatile media and volatile media and may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 606 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in main memory 1016, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

Embodiments of the present disclosure include various steps, which are described in this specification. The steps may be performed by hardware components or may be embodied in machine-executable instructions, which may be used to cause a general-purpose or special-purpose processor programmed with the instructions to perform the steps. Alternatively, the steps may be performed by a combination of hardware, software and/or firmware.

It should be understood from the foregoing that, while particular aspects have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A device for monitoring subsurface conditions, the device comprising:
   a data collector comprising at least one hardware processor and at least one memory to store executable instructions; and
   a plurality of sensors in communication with the data collector deployed in a subsurface of a monitored area, each of the plurality of sensors obtaining an environmental measurement of the subsurface of the monitored area and transmitting, via a communication wire, the environmental measurement to the data collector, a subset of the plurality of sensors grouped together as a group of sensors comprising a temperature sensor, a water-level sensor, and an oxidation reduction potential sensor;
   wherein the instructions, when executed by the at least one processor, are configured to:
      package a plurality of the environmental measurements received from the plurality of sensors into one or more transmission packets; and
      wirelessly transmit the one or more transmission packets to a monitoring system, the monitoring system in communication with a user interface for displaying the environmental measurements comprising a time series of contoured natural source zone (NSZD) rates over an overhead map of the monitored area, the time series of contoured natural source zone (NSZD) rates based on a plurality of temperature measurements of the subsurface of the monitored area.

2. The device of claim 1 further comprising:
   a conduit connected between the data collector and the plurality of sensors, the conduit housing the communication wire.

3. The device of claim 1 further comprising:
   a second subset of the plurality of sensors grouped together as a second group of sensors comprising a second temperature sensor, a second water-level sensor, and a second oxidation reduction potential sensor.

4. The device of claim 3, wherein the second group of sensors transmits environmental measurements obtained by the second group of sensors on the communication wire, the second group of sensors associating a unique address with the environmental measurements obtained by the second group of sensors, the unique address assigned to the second group of sensors by the data collector.

5. The device of claim 3, wherein the second group of sensors transmits environmental measurements obtained by the second group of sensors to the data collector on a second communication wire different than the communication wire.

6. The device of claim 1, wherein the plurality of sensors further comprises a pH sensor and a soil moisture sensor.

7. The device of claim 1 further comprising:
   a power source comprising a battery in electrical communication with a solar cell, the solar cell recharging the battery.

8. The device of claim 1, wherein each of the plurality of sensors further transmit via the communication wire, an operational indicator of an operational status of a corresponding sensor and wherein the instructions, when executed by the at least one processor, are further configured to:
   package a plurality of operational indicators received from the plurality of sensors into one or more operational packets; and
   wirelessly transmit the one or more operational packets to the monitoring system in communication with the user interface for displaying the plurality of operational indicators.

9. The device of claim 1, wherein displaying of the environmental measurements comprises a simulated groundwater flow direction over an overhead map of the monitored area, the simulated groundwater flow direction based on a plurality of water-level measurements of the subsurface of the monitored area.

10. A method for monitoring subsurface conditions at a pollution site, the method comprising:
   receiving, via a plurality of sensors in communication with a data collector of a sensor array deployed in a subsurface of a monitored area, a plurality of environmental measurements of the subsurface of the monitored area, each of the plurality of sensors obtaining a corresponding environmental measurement of the subsurface of the monitored area and transmitting, via a communication wire, the environmental measurement to the data collector, wherein a subset of the plurality of sensors are grouped together as a group of sensors comprising a temperature sensor, a water-level sensor, and an oxidation reduction potential sensor;
   generating one or more visualizations of the plurality of environmental measurements for display on a display device; and
   transmitting, to a computing device and via a network connection, the one or more visualizations of the plurality of environmental measurements for display in a user interface executed by the computing device, the plurality of environmental measurements comprising a time series of contoured natural source zone rates over an overhead map of the monitored area, the time series of contoured natural source zone rates based on a plurality of temperature measurements of the subsurface of the monitored area.

11. The method of claim 10 further comprising:
receiving, via the computing device, one or more configuration requests for configuring an operation of the sensor array;
generating one or more configuration instructions for configuring the operation of the data collector; and
transmitting, via the network connection, the one or more configuration instructions to the data collector.

12. The method of claim 10 further comprising:
receiving, via the data collector of the sensor array deployed in the subsurface of the monitored area, a plurality of operational indicators associated with the operation of the plurality of sensors;
generating a dashboard comprising a visualization of the plurality of operational indicators for display on the display device; and
transmitting, to the computing device, the dashboard for display in the user interface.

13. The method of claim 10, wherein the one or more visualizations of the plurality of environmental measurements comprises a simulated groundwater flow direction over an overhead map of the monitored area, the simulated groundwater flow direction based on a plurality of water-level measurements of the subsurface of the monitored area.

14. The method of claim 10, wherein the one or more visualizations of the plurality of environmental measurements comprises a time series of contoured selected oxidation reduction potential values over an overhead map of the monitored area, the time series of contoured selected oxidation reduction potential values based on a plurality of oxidation reduction potential measurements of the subsurface of the monitored area.

15. The method of claim 10, wherein the sensor array comprises a plurality of groups of sensors, the plurality of groups of sensors forming a vertical and horizontal fence within the subsurface of the monitored area for obtaining the corresponding environmental measurement of the subsurface of the monitored area.

16. A system for monitoring subsurface conditions, the system comprising:
a sensor array deployed at a monitored area comprising:
a data collector comprising a wireless communication unit; and
a plurality of sensors in communication with the data collector via a communication wire disposed within a conduit, each of the plurality of sensors obtaining an environmental measurement of the subsurface of the monitored area and transmitting the environmental measurement to the data collector, the plurality of sensors comprising a temperature sensor, a water-level sensor, and an oxidation reduction potential sensor; and
a monitoring system of a computing network, the monitoring system comprising a processor and at least one memory to store instructions that are configured to, when executed by the processor to:
receive, via the wireless communication unit of the data collector, the environmental measurement of the subsurface of the monitored area;
generate one or more visualizations of the environmental measurement for display on a display device; and
transmit, to a computing device and via a network connection, the one or more visualizations of the environmental measurement for display in a user interface executed by the computing device, the environmental measurement comprising a time series of contoured natural source zone rates over an overhead map of the monitored area, the time series of contoured natural source zone rates based on a plurality of temperature measurements of the subsurface of the monitored area.

17. The system of claim 16, wherein each of the plurality of sensors further transmit via the communication wire, an operational indicator of an operational status of a corresponding sensor and the data collector, via the wireless communication unit, transmits a plurality of operational indicators to the monitoring system.

18. The system of claim 16, wherein the plurality of sensors further comprises a pH sensor and a soil moisture sensor.

* * * * *